(12) United States Patent
Penaz

(10) Patent No.: US 9,480,369 B2
(45) Date of Patent: Nov. 1, 2016

(54) DISPOSABLE HAND CLEANING GLOVE AND METHOD

(71) Applicant: Ivar Penaz, Chicago, IL (US)

(72) Inventor: Ivar Penaz, Chicago, IL (US)

( * ) Notice: Subject to any disclaimer, the term of this patent is extended or adjusted under 35 U.S.C. 154(b) by 290 days.

(21) Appl. No.: 14/253,611

(22) Filed: Apr. 15, 2014

(65) Prior Publication Data

US 2015/0289728 A1    Oct. 15, 2015

(51) Int. Cl.
| | |
|---|---|
| *A47L 13/19* | (2006.01) |
| *A47L 13/18* | (2006.01) |
| *A47K 7/03* | (2006.01) |
| *A61Q 19/10* | (2006.01) |
| *A41D 19/00* | (2006.01) |
| *B08B 3/08* | (2006.01) |
| *A61Q 17/00* | (2006.01) |
| *A61K 8/02* | (2006.01) |

(52) U.S. Cl.
CPC .................. *A47K 7/03* (2013.01); *A47L 13/18* (2013.01); *A47L 13/19* (2013.01); *A61K 8/0208* (2013.01); *A61Q 17/005* (2013.01); *A61Q 19/10* (2013.01); *B08B 3/08* (2013.01); *A41D 19/0024* (2013.01)

(58) Field of Classification Search
CPC ............... A47K 7/03; A41D 19/0024; A41D 19/0044; A61Q 17/005; A61Q 19/00; A61Q 19/10; A61K 8/0208; A47L 13/18; A47L 13/19
USPC .............................................. 134/6; 15/104.3
See application file for complete search history.

(56) References Cited

U.S. PATENT DOCUMENTS

| | | | |
|---|---|---|---|
| 2007/0192932 A1* | 8/2007 | Wells ................. | A41D 19/0055 2/162 |
| 2015/0150322 A1* | 6/2015 | Fraga-Rosenfeld | A41D 19/0082 134/22.1 |

* cited by examiner

*Primary Examiner* — Saeed T Chaudhry
(74) *Attorney, Agent, or Firm* — Erickson Law Group, PC

(57) ABSTRACT

A disposable hand cleaning glove and method is provided. The glove has a hand portion and a sleeve portion. The hand portion has an interior and an access opening configured to receive a human hand into the interior. The interior has a hand cleaning substance. The sleeve portion is connected to the hand portion about the access opening of the hand portion. The sleeve portion has an absorbent material.

19 Claims, 2 Drawing Sheets

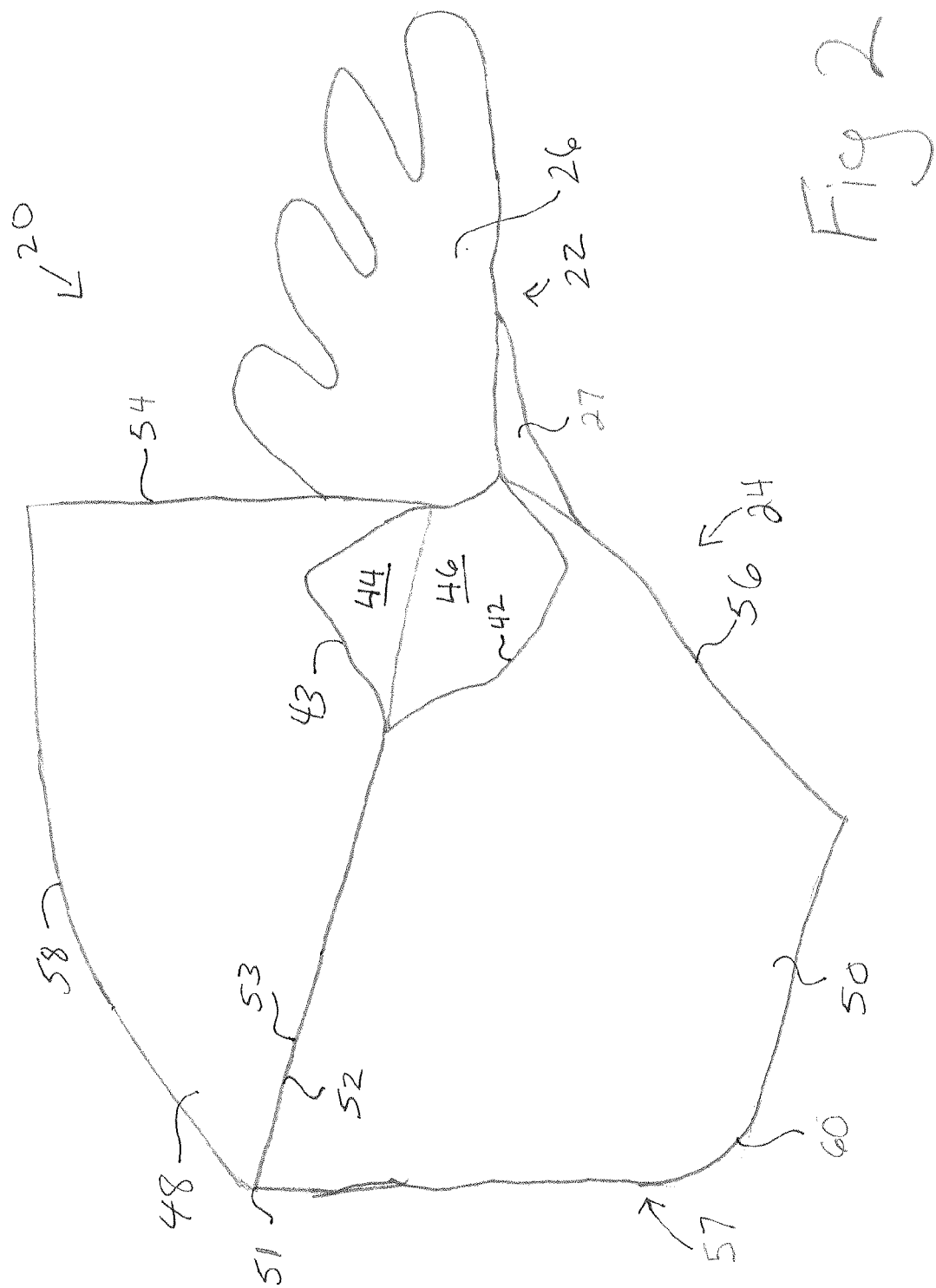

DISPOSABLE HAND CLEANING GLOVE AND METHOD

FIELD OF THE INVENTION

This invention relates in general to disposable cleaning gloves.

BACKGROUND OF THE INVENTION

The need to clean one's hands arises in many situations. In some such situations, the there is no source of water located near at the time when the person needs or desires to clean his or her hands. Even if water is near, there might not be soap or other cleaner at the source of the water. Further, even if soap and water are within walking distance of a person, the person may desire a way to clean his or her hands at a particular location without moving to the water source.

Dispensers for hand sanitizer, which do not require water to carry out the cleaning, have been placed in locations were cleaning is desired but the water source is not within convenient reach. The present inventor recognized that such sanitizer dispensers suffer from the drawback of not being accompanied with a means of drying one's hands. Therefore, a user is required to wait until the hand sanitizer has dried, which may be inconvenient. Further, hand sanitizer does not work to remove all kinds of substances from one's hands. The process of removing some substances from a human hand can benefit from rubbing friction beyond what can be achieved by rubbing one's hands together.

The present inventor recognized the need for a faster and more convenient device and method for cleaning one's hands. The present inventor recognized the need for a self-contained device for cleaning one's hands. The present inventor recognized the need for a device that has a hand cleaning substance pre-applied within. The present inventor recognized the need for a device that can apply a cleaning substance about the user's entire hand. The present inventor recognized the need for a device where the cleaning substance is separated from the external environment. The present inventor recognized the need for a disposable hand cleaning device. The present inventor recognized the need for a device that contains a means for both applying a cleaning substance to one's hand and removing the cleaning substance remaining on one's hand.

SUMMARY OF THE INVENTION

A disposable hand cleaning glove is disclosed. The glove has a hand portion and a sleeve portion. The hand portion has an interior and an access opening configured to receive a human hand into the interior. The interior has a hand cleaning substance. The sleeve portion is connected to the hand portion about the access opening of the hand portion. The sleeve portion has an absorbent material.

The hand portion has one or more interior surfaces. The one or more interior surfaces have the hand cleaning substance in the form of a thin film applied thereon. In some embodiments all of the one or more interior surfaces have the hand cleaning substance in the form of a thin film applied thereon.

The hand portion is a flexible plastic. The absorbent material of the sleeve is an absorbent paper. The hand portion is sized to be larger than the wearer's hand to allow the hand portion to be movable relative to the wearer's hand.

In some embodiments the cleaning substance is soap. In some embodiments, the cleaning substance is hand sanitizer. In some embodiments, the cleaning substance is a liquid soap.

In some embodiments, the sleeve provides the only access to an interior of the hand portion through the access opening.

A method of cleaning a human hand is disclosed. A user slides the user's hand through a sleeve portion of a glove into a hand portion of the glove. The hand is cleaned by moving the hand portion of the glove relative to the user's hand or by moving the user's hand relative to the hand portion of the glove to apply a cleaning substance located within the hand portion to the user's hand. Then the hand is withdrawn from at least the hand portion. The cleaning substance remaining on the user's hand is absorbed by the sleeve.

In some embodiments, the absorbing occurs before, after, or both before and after the user's hand is withdrawn from the sleeve by rubbing the user's hand with the sleeve.

Numerous other advantages and features of the present invention will become readily apparent from the following detailed description of the invention and the embodiments thereof, from the claims, and from the accompanying drawings.

BRIEF DESCRIPTION OF THE DRAWINGS

FIG. 2 is a perspective view of the glove of FIG. 1 with a sleeve portion at least partially open.

DETAILED DESCRIPTION

Figure 1:
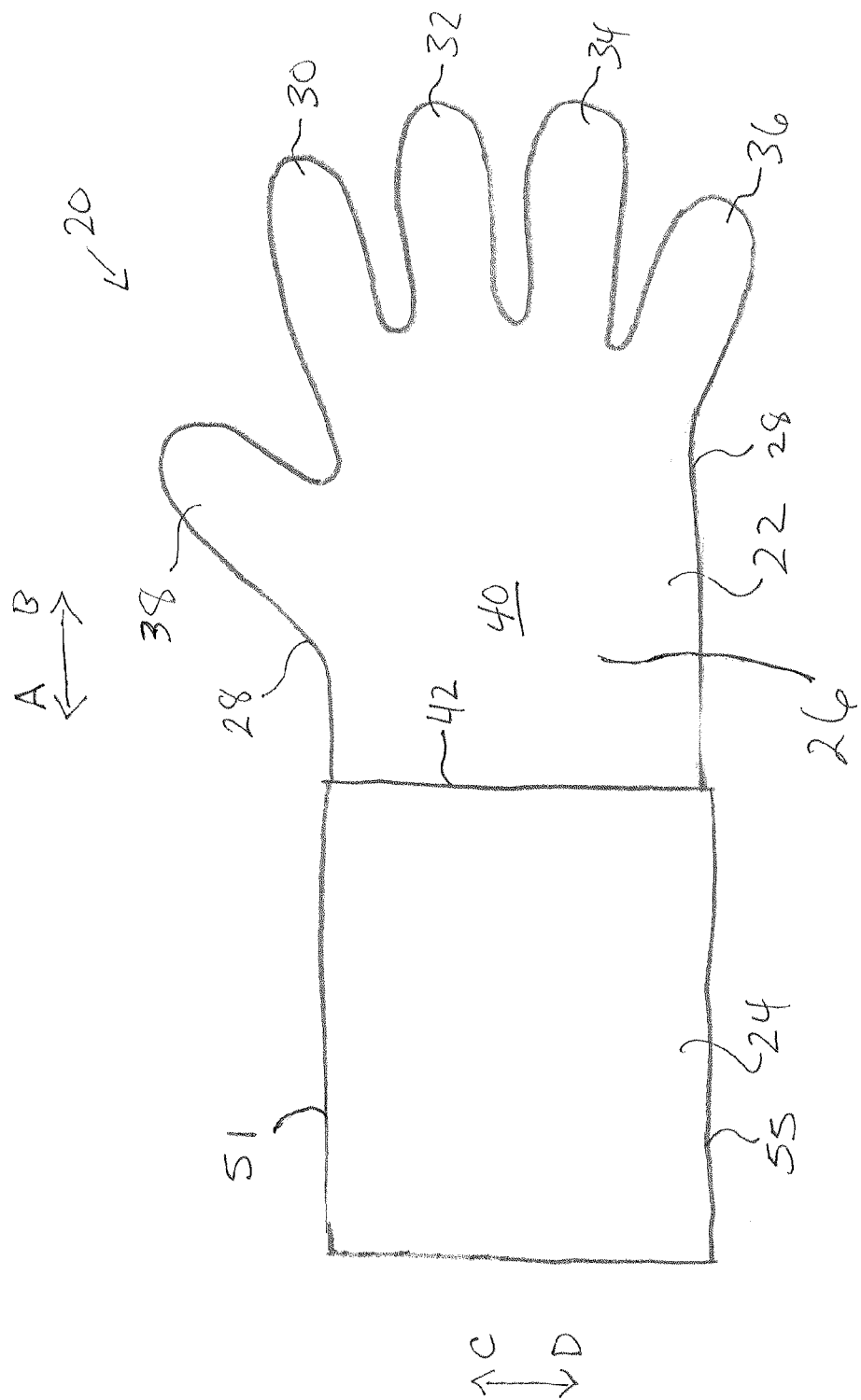
FIG. 1 is a palmar view of one embodiment of a glove of the invention.

The following description is presented to enable any person skilled in the art to make and use the invention. For the purposes of explanation, specific nomenclature is set forth to provide a plural understanding of the present invention. While this invention is susceptible of embodiment in many different forms, there are shown in the drawings, and will be described herein in detail, specific embodiments thereof with the understanding that the present disclosure is to be considered as an exemplification of the principles of the invention and is not intended to limit the invention to the specific embodiments illustrated.

A glove 20 of the invention is disclosed. The glove comprises a hand portion 22 and a sleeve portion 24. The hand portion 22 comprises at least a palmar portion 26 and a dorsal portion 27. The dorsal portion is configured to cover the dorsal side of a human hand. The palmar portion is configured to cover the palmar side of a human hand.

In some embodiments, the dorsal portion can be joined to the palmar portion along a peripheral edge 28 that extends about the hand portion. In some embodiments, the dorsal and palmer portions are formed as one unit.

The hand portion has four finger portions 30, 32, 34, 36, a thumb portion 38, a palm area 40 on the palmar portion 26, and a complementary area on the opposite dorsal portion 27. In some embodiments, ends of the finger portions are cut off to allow a user's finger to extend beyond the end of the finger portions. In some embodiments, the hand portion is formed as a mitten comprising a thumb portion and one finger receiving area for all the fingers.

As shown in FIG. 2, each of the palmar and dorsal portions 26, 27 comprise an interior surface 44, 46 respectively, that extends along the entire palmar and dorsal portions, respectively, including the finger and thumb portions. The interior surfaces 44, 46 face each other. The interior surface 44 of the palmar portion 26 is configured to contact the palmar side of the hand. The interior surface 46 of the dorsal portion 27 is configured to contact the dorsal side of the hand.

At a wrist end 42 of the hand portion opposite the finger portions the hand portion is joined to the sleeve portion 24. The wrist end 42 of the hand portion joins with the wrist end 43 of the sleeve portion. The joining may be achieved by the use of an adhesive, such as glue, applied about the entire perimeter of the wrist end 42 and/or 43, or one or more portions thereof. When adhesive is applied about the entire perimeter, the sleeve provides the only access to the interior of the hand portion. In some embodiments, the hand portion is connected to the sleeve portion with a connector, such as a staple.

The sleeve portion has an anterior portion 48 and a posterior portion 50. The anterior portion joins with the palmer portion of the hand portion. The posterior portion joins with the dorsal portion of the hand portion. Opposite sides 52, 56 of the posterior portion 50 are joined with opposite sides 53, 54 of the anterior portion to form connection seams 51, 55. In some embodiments, one of the seams is left open so that the corresponding opposite sides 54, 56 are not connected to each other. In some embodiments, both opposite sides 52, 53, and 54, 56 are joined to each other. In some embodiments, the anterior portion 48 and a posterior portion 50 are formed of one continuous piece of material and one or both joints are eliminated. The sleeve provides a hollow interior to receive a users hand and forearm there through and therein, respectively.

The entry opening 57 exists opposite the wrist end 43 of the sleeve portion as the forearm ends 58, 60 are disconnected from each other. The entry opening provides access to the interior of the sleeve portion and the hand portion.

The interior surfaces 44, 46 of the hand portion are coated with a cleaning substance for cleaning the wearer's hands. In some embodiments, the cleaning substance comprises a soap.

In some embodiments, the soap is a thin film applied to all of or a part of the interior surfaces 44, 46. In some embodiments, the soap comprises animal or vegetable fat/oil, and/or water. In some embodiments the soap comprises sodium tallowate, sodium cocoate, or sodium palmate. Lye (sodium hydroxide) may be used to bring about a saponification reaction in the formation of the soap. The fat can comprise coconut oil, soybean oil, palm oil, tallow, and/or lard. In some embodiments, the soap comprises glycerin, hydrogenated tallow acid, and/or an emollient additive, such as jojoba oil or shea butter. In some embodiments, the soap comprises a fragrance and/or a color dye. In some embodiments, the soap comprises an antioxidant agent such as Pentaerythrityl tetraditbutyl hydroxyhydrocinnamate or butylated hydroxytoluene. In some embodiments, the cleaning substance comprises isoparaffin, fatty acids, surfactants, and lanolin.

In some embodiments, the cleaning substance comprises an anti-bacterial ingredient, or an anti-microbial ingredient.

In some embodiments, the interior surfaces 44, 46 of the hand portion are coated with a skin moisturizing substance. In some embodiments, the skin moisturizing substance is combined with the cleaning substance.

In some embodiments, the cleaning substance comprises a hand sanitizer or antiseptic. Such a sanitizer or antiseptic comprises an alcohol, such as isopropanol, ethanol, n-propanol. In some embodiments, the sanitizer is a non-alochol based sanitizer comprising benzalkonium chloride, the chlorinated aromatic compound triclosan, or povidone-iodine.

In some embodiments, the hand portion comprises flexible plastic. The plastic may be a thin plastic film. In some embodiments, the thin plastic film comprises polyethylene, such as low-density polyethylene or linear low-density polyethylene. The flexible plastic allows the wearer to manipulate the wearer's hand in a full range of motion. In some embodiments, the hand portion is a high density polyethylene.

The sleeve portion comprises a liquid absorbent material. In some embodiments, the liquid absorbent material is a liquid absorbent paper. The absorbent paper comprises cellulose fibers that liquids cling to when encountered. The absorbent paper is permeable and porous to allow liquid to pass through and be absorbed. The paper comprises plant based materials from cotton or wood. The paper may comprise pockets of space, created by creping, to increase strength and absorbency. The paper may comprise embossing that stamps the paper with a pattern or design having raised portions that trap liquid. The paper may comprise one, two, three, or more plies or layers.

In operation, the user inserts the user's hand in the entry opening 57, the user draws the glove in the direction A to cause the user's hand to pass through the sleeve portion and into the hand portion until at least one of the user's fingers or thumb reach the end of the finger portions 30, 32, 34, 36 or a thumb portion 38 so that the glove is in the fully on position relative to the user. In some usages, the glove need not be in the fully on position but only needs to be to some extent in the hand portion. For example, if user only desires the user's fingers to be cleaned, when the user might desire to move the user's fingers into the hand portion but not the remaining part of the user's hand.

The glove provides an interior space between the palmar portion 26 and an dorsal portion 27 that is at least slightly larger than the space occupied by the wearer's hand, so that the hand portion can move relative to the user's hand, or vise versa, in one or more or in any direction. The user can then rub his gloved hand on his ungloved hand, or if two gloves are used against his other gloved hand, or against another object, thing, or body part. The movement will cause the interior surfaces 44, 46 to rub against the wearing hand of the wearer and the cleaning substance will therefore be applied to the wearing hand. The duration and vigor with which the rubbing occurs will determine how much the cleaning substance is worked against the skin of the wearer's hand and how much cleaning or sanitizing occurs.

The presence of the cleaning substance of on all of the interior surfaces of the hand portion allows a uniform application of the cleaning substance about the entire surface of the wearer's hand.

Once the user has worked the cleaning substance against the wearer's hand for the desired duration via movement of the hand portion relative to the worn hand, the user will draws the user's hand back in the direction A into the sleeve portion, without withdrawing the hand completely from the sleeve. Then the user rubs the sleeve about the hand in one or more direction, such as in back and forth directions A and B of FIG. 1. Any and all other directions of rubbing, such as circular or back and forth in the directions C and D may be employed by the user. The rubbing of the sleeve on the hand causes the liquid absorbing material of the sleeve to absorb and remove the cleaning substance from the user's hand. The amount of cleaning substance that is removed, depends on the thoroughness and duration of the rubbing employed by the user.

In some methods, the user can withdraw the user's hand entirely and use the sleeve portion as one would a traditional paper towel to remove the cleaning substance. In this method, the exterior of the sleeve portion may be in main contact with the hand in need of the cleaning substance to be removed.

From the foregoing, it will be observed that numerous variations and modifications may be effected without departing from the spirit and scope of the invention. It is to be understood that no limitation with respect to the specific apparatus illustrated herein is intended or should be inferred.

The invention claimed is:

1. A disposable hand cleaning glove, comprising:
   a hand portion comprising an interior and an access opening, the interior comprising a soap; and,
   a sleeve portion connected to the hand portion about the access opening of the hand portion, the sleeve portion comprising an absorbent material.

2. The glove of claim 1, wherein the hand portion comprises one or more interior surfaces, the one or more interior surfaces comprise the soap in the form of a thin film applied thereon.

3. The glove of claim 1, wherein the hand portion comprises one or more interior surfaces, all of the one or more interior surfaces comprise the soap in the form of a thin film applied thereon.

4. The glove of claim 1, wherein the soap is a liquid soap.

5. The glove of claim 1, wherein the hand portion comprises a flexible plastic.

6. The glove of claim 1, wherein the absorbent material is an absorbent paper.

7. The glove of claim 1, wherein the sleeve provides the only access to the interior of the hand portion through the access opening.

8. The glove of claim 1, wherein the hand portion is sized to be larger than the wearer's hand to allow the hand portion to be movable relative to the wearer's hand.

9. The glove of claim 1, wherein
   the hand portion comprises one or more interior surfaces defining the interior, all of the one or more interior surfaces comprise the soap in the form of a thin film applied thereon;
   the hand portion comprises a flexible plastic;
   the absorbent material is an absorbent paper;
   the sleeve connects about the entire perimeter of the access opening;
   the interior of the hand portion is enclosed except for the access opening; and,
   the hand portion comprises a plurality of finger portions and a thumb portion.

10. The glove of claim 1, wherein the interior comprises a skin moisturizing substance.

11. The glove of claim 1, wherein the hand portion comprises a thumb portion, and a plurality of finger portions or a mitten portion for receiving multiple fingers.

12. The glove of claim 1, wherein the sleeve portion is connected to the hand portion with an adhesive.

13. A method of cleaning a human hand, comprising the steps of:
    sliding a user's hand through a sleeve portion of a glove into a hand portion of the glove;
    cleaning the user's hand by moving the hand portion of the glove relative to the user's hand or by moving the user's hand relative to the hand portion of the glove to apply a cleaning substance located within the hand portion to the user's hand;
    withdrawing the hand from at least the hand portion; and
    absorbing the cleaning substance remaining on the user's hand with the sleeve.

14. The method of claim 13, wherein the step of absorbing comprises the step of absorbing the cleaning substance remaining on the user's hand with the sleeve before the user's hand is withdrawn from the sleeve by rubbing the user's hand with the sleeve.

15. The method of claim 13, wherein the step of absorbing comprises the step of absorbing the cleaning substance remaining on the user's hand with the sleeve after the user's hand is withdrawn from the sleeve by rubbing the user's hand with the sleeve.

16. The method of claim 13, wherein the step of absorbing comprises the steps of:
    absorbing at least a portion of the cleaning substance remaining on the user's hand with the sleeve before the user's hand is withdrawn from the sleeve by rubbing the user's hand with the sleeve; and
    absorbing the cleaning substance remaining on the user's hand with the sleeve after the user's hand is withdrawn from the sleeve by rubbing the user's hand with the sleeve.

17. The method of claim 13, wherein the step of absorbing is further defined in that the sleeve comprises an absorbent paper and the absorbent paper of the sleeve absorbs the cleaning substance from the user's hand.

18. The method of claim 13, wherein the step of cleaning comprises rubbing the hand portion having the cleaning substance, in the form of a thin film on one or more interior walls of the hand portion, on the user's hand.

19. The method claim 13, comprising the step of disposing of the glove after the step of absorbing.

* * * * *